United States Patent

Baasner

Patent Number: 4,774,358
Date of Patent: Sep. 27, 1988

[54] CYCLOPROPYLAMINES CONTAINING TRIFLUOROMETHYL GROUPS

[75] Inventor: Bernd Baasner, Leverkusen, Fed. Rep. of Germany

[73] Assignee: Bayer Aktiengesellschaft, Leverkusen, Fed. Rep. of Germany

[21] Appl. No.: 27,703

[22] Filed: Mar. 19, 1987

[30] Foreign Application Priority Data

Apr. 4, 1986 [DE] Fed. Rep. of Germany ....... 3611196

[51] Int. Cl.$^4$ .............................................. C07C 87/34
[52] U.S. Cl. ......................................................... 564/1
[58] Field of Search ............................................ 564/1

[56] References Cited

U.S. PATENT DOCUMENTS 4,668,830  5/1987  Desbois ................................... 564/1
4,705,788  11/1987  Schriewer et al. ..................... 564/1

OTHER PUBLICATIONS

Chemical Abstracts published by the American Chemical Society, vol. 88, Jun. 12–Jun. 26 (Abstracts 170497-202625), 1978, P 1537, p. 1; 1-Pharmacodynamics; p. 702, 24-Alicyclic Compounds.
The Journal of Organic Chemistry, vol. 27; Jan.-Apr. 1962, pp. 1-1492), The Chemistry of Sulfur Tetrafluoride. IX Reaction with Amino Acids in Hydrogen Fluoride[1], pp. 1406'1409.
Journal of Organic Chemistry, 27, 1406 (1962).
J. Chem. Soc., 2119-2132 (1960).
Synthesis, 46 (1978).
Coll. Czech. Chem. Comm., 47, 2291-2305 (1982).

Primary Examiner—Glennon H. Hollrah
Assistant Examiner—John A. Sopp
Attorney, Agent, or Firm—Sprung Horn Kramer & Woods

[57] ABSTRACT

A cyclopropylamine of the formula

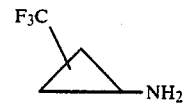

and a process for producing the same by reacting a cyclopropylcarboxylic acid amine of the formula

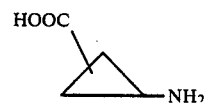

with sulphur tetrafluoride in anhydrous hydrogen fluoride. The cyclopropylamine is useful in the preparation of benzoic acid amides which have an insecticidal action.

3 Claims, No Drawings

CYCLOPROPYLAMINES CONTAINING TRIFLUOROMETHYL GROUPS

BACKGROUND OF THE INVENTION

Field of the Invention

The present Application relates to new cyclopropylamines containing trifluoromethyl groups and processes for their preparation.

SUMMARY OF THE INVENTION

New cyclopropylamines containing trifluoromethyl groups, of the formula (I)

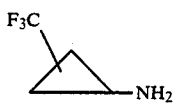

have been found.

It has furthermore been found that the cyclopropylamines of the formula (I)

can be prepared by a process in which cyclopropanecarboxylic acid amines of the general formula (II)

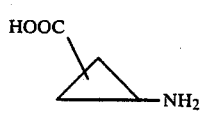

are reacted with sulphur tetrafluoride in anhydrous hydrogen fluoride.

DETAILED DESCRIPTION OF THE INVENTION

The new compounds of the general formula (I) are suitable as useful intermediate products for syntheses in organic chemistry. The new compounds of the formula (I) are particularly suitable for the preparation of new benzoic acid amides which have an insecticidal action. The following synthesis may be mentioned here as an example:

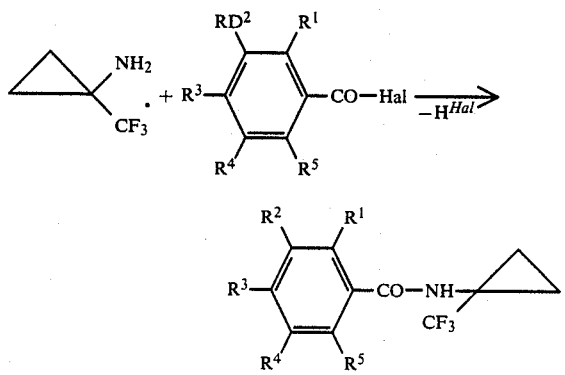

wherein the substituents $R^1$, $R^2$, $R^3$, $R_4$ and $R^5$ can be identical or different and represent hydrogen, halogen, nitro, alkyl, halogenoalkyl, halogenoalkoxy or halogenoalkylthio.

The following compounds of the general formula (I) are possible: 1-trifluoromethyl-cyclopropylamine and 2-trifluoromethyl-cyclopropylamine.

If 1-amino-cyclopropanecarboxylic acid is used as the starting substance, the reaction can be represented as follows:

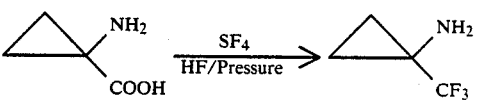

The reaction of the cyclopropanecarboxylic acids of the formula (II) with sulphur tetrafluoride to introduce the trifluoromethyl group is carried out in anhydrous hydrogen fluoride by a process which is known per se (in this context, see *Journal of Organic Chemistry*, 27, 1406 (1962)).

For this, the aminocarboxylic acids of the general formula (II) are reacted with sulphur tetrafluoride in hydrogen fluoride in a steel stirred autoclave at 100° to 180° C., preferably at 120° to 160° C., under the autogenous pressure for about 4 to 12 hours, preferably 6 to 10 hours. 2 to 10 mol, preferably 2 to 5 and particularly preferably 2 to 3 mol, of sulphur tetrafluoride and 3 to 200, preferably 3 to 100 and especially preferably 3 to 60 mol of hydrogen fluoride are employed per mol of aminocarboxylic acid. The processes usually employed are used for working up the reaction mixture. Thus, the volatile constituents can be distilled off, the crude product can be rendered alkaline with aqueous alkali metal hydroxide solution and the product can be separated off by distillation, extraction or steam distillation.

If, for example, the amine is separated off by steam distillation, the product can be isolated from the distillate, if it separates out as a second phase, by phase separation. However, the distillate can also be acidified with hydrochloric acid. The hydrochloride of the amine of the general formula (I) is then obtained in a pure form by concentration to dryness. The free amine of the general formula (I) can be obtained therefrom by treatment with an alkali for neutralization of the hydrochloric acid from the hydrochloride. The amine is obtained in a pure form by distillation from this crude mixture. However, it is also possible for the amine of the general formula (I) to be extracted from this crude mixture with an inert organic solvent and for the amine to be isolated from this extract by distillation.

The cyclopropanecarboxylic acid amines of the general formula (II) are known (for example *J. Chem. Soc.*, 1960, 2119-2132; ibid. 1962, 3977-3980; *Synthesis*, 1978, 46; and *Coll. Czech. Chem. Comm.*, 47, 2291-2305/(1982)) or they can be prepared by a known process.

PREPARATION EXAMPLES

Example 1

1-Trifluoromethly-cyclopropylamine hydrochloride 40 g (0.4 mol) of cyclopropyl-1-aminocarboxylic acid are reacted with 100 g of sulphur tetrafluoride and 50 ml of HF in a V$_4$A stirred autoclave at 120° C. under the autogenous pressure (30→25 bar) for 8 hours. After the volatile constituents have been distilled off, the mixture is rendered alkaline with 45% strength sodium hydroxide solution and the product is then separated off by steam distillation. The steam distillate is acidified with concentrated hydrochloric acid. After concentration and drying, 40 g (62%) of 1-trifluoromethyl-cyclopropylamine are isolated as the hydrochloride (Fp.: >260° C.).

Example 2

1-Trifluoromethyl-cyclopropylamine 44 g (0.22 mol) of 20% strength aqueous sodium hydroxide solution are added dropwise to 32.4 g (0.2 mol) of 1-trifluoromethylcyclopropylamine hydrochloride from Example 1 at an oil bath temperature of 80°–90° C. in the course of about 15 minutes. The amine liberated is distilled off at the same time. After drying over magnesium sulphate, the product is redistilled. 22.2 g (89%) of 1-trifluoromethyl-cyclopropylamine, boiling point: 50° to 52° C., $n_D^{20}$: 1.3483 are obtained as the product.

It will be appreciated that the instant specification and claims are set forth by way of illustration and not limitation, and that various modifications and changes may be made without departing from the spirit and scope of the present invention.

What is claimed is:

1. A cyclopropylamine of the formula (I)

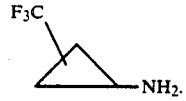

2. A cyclopropylamine according to claim 1, wherein the cyclopropylamine is 1-trifluoromethyl-cyclopropylamine.

3. A cyclopropylamine according to claim 1, wherein the cyclopropylamine is 2-trifluoromethyl-cyclopropylamine.

* * * * *